United States Patent

Chassot et al.

(10) Patent No.: US 6,875,873 B2
(45) Date of Patent: Apr. 5, 2005

(54) 1,4-DIAMINO-2-(THIAZOL-2-YL)BENZENE DERIVATIVES, AND DYES CONTAINING SAID COMPOUNDS

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/203,597

(22) PCT Filed: Sep. 10, 2001

(86) PCT No.: PCT/EP01/10407

§ 371 (c)(1),
(2), (4) Date: Aug. 9, 2002

(87) PCT Pub. No.: WO02/057243

PCT Pub. Date: Jul. 25, 2002

(65) Prior Publication Data

US 2003/0115683 A1 Jun. 26, 2003

(30) Foreign Application Priority Data

Jan. 18, 2001 (DE) .......................................... 101 02 084

(51) Int. Cl.[7] ................... C07D 277/22; C07D 277/28; C09B 67/00
(52) U.S. Cl. ........................... 548/203; 548/205; 8/571
(58) Field of Search ................................ 548/203, 205; 8/571

(56) References Cited

U.S. PATENT DOCUMENTS

| 4,828,568 A | 5/1989 | Konrad |
| 6,042,620 A | 3/2000 | Braun et al. |
| 6,132,475 A | 10/2000 | Chassot et al. |

FOREIGN PATENT DOCUMENTS

| DE | 21 25 193 A | 11/1972 |
| DE | 198 12 059 C | 9/1999 |
| DE | 299 12 882 U1 | 11/1999 |
| DE | 201 08 704 U | 9/2001 |
| EP | 0 513 387 A1 | 11/1992 |
| EP | 1 052 252 A | 11/2000 |
| JP | 5-155870 | 6/1993 |
| WO | 99/59527 | 11/1999 |

OTHER PUBLICATIONS

Protective Groups:, Organic Synthesis, Chapter 7, Wiley Interscience, Protectiontion for the Amino Groups, 1991, PP 309–330.

J. M. Tour and J.J.S. LMABA: "Imine–Bridged Planar Poly . . . ", In J. Am. Chem.Soc. 1994, 116, pp. 11723–11736.

*Primary Examiner*—Rita Desai
*Assistant Examiner*—Robert Shiao
(74) *Attorney, Agent, or Firm*—Michael J. Striker

(57) ABSTRACT

1,4-Diamino-2-(thiazol-2-yl)benzene derivatives of general formula (I) and the physiologically tolerated, water-soluble salts thereof:

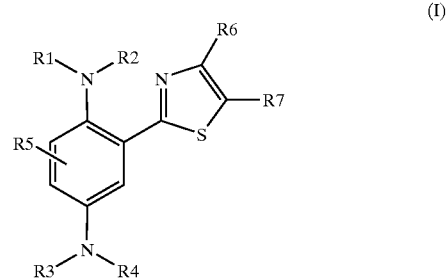

and agents containing these compounds, for oxidative dyeing of keratin fibers.

14 Claims, No Drawings

1,4-DIAMINO-2-(THIAZOL-2-YL)BENZENE DERIVATIVES, AND DYES CONTAINING SAID COMPOUNDS

The invention relates to novel 1,4-diamino-2-(thiazol-2-yl)benzene derivatives and to colorants for keratin fibers containing these compounds.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diaminopyrazole, and suitable couplers are, for example, resorcinol, 4-chlororesorcinol, 1-naphthol, 3-aminophenol, m-phenylenediamine, 2-amino-4-(2'-hydroxyethyl) aminoanisole, 1,3-diamino-4-(2'-hydroxyethoxy)benzene and 2,4-diamino-5-fluorotoluene.

The oxidation dyes used for dyeing human hair must meet numerous requirements in addition to that of being able to produce colorations of the desired intensity. For example, these dyes must be harmless from a toxicological and dermatological standpoint, and the hair colorations obtained must have good light fastness, resistance to permanent waving, acid fastness and rubbing fastness. In any case, however, in the absence of exposure to light, rubbing and chemicals, such colorations must remain stable over a period of at least 4 to 6 weeks. Moreover, by combining appropriate developers and couplers, it must be possible to create a wide range of different color shades.

In German Patent 198 12 059 and German Utility Patent 299 12 882, it is recommended to use as developers in oxidative colorants novel 2,5-diamino-1-(2-thienyl)benzenes in place of the long-known p-phenylenediamines.

The need, however, continued to exist for novel developers meeting the requirements placed on oxidation dye precursors to a major degree.

Surprisingly, in this respect we have now found that novel 1,4-diamino-2-(thiazol-2-yl)benzene derivatives of general formula (I) meet the requirements placed on developers to an especially high degree. In fact, by use of these developers and with most known couplers, color shades of high color intensity are obtained which are unusually light-fast and wash-fast.

Hence, the object of the present invention are 1,4-diamino-2-(thiazol-2-yl)benzene derivatives of general formula (I) or the physiologically tolerated, water-soluble salts thereof:

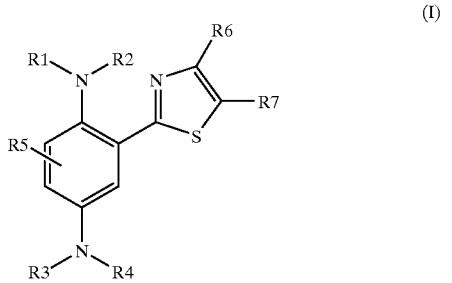

(I)

wherein

R1, R2, R3 and R4 independently of each other denote hydrogen, a $C_1$–$C_6$-alkyl, $C_2$–$C_4$-hydroxyalkyl, $C_3$–$C_4$-dihydroxyalkyl or $C_2$–$C_4$-alkoxy-($C_1$–$C_2$)-alkyl group or R1 and R2 or R3 and R4 form a four-membered to eight-membered aliphatic ring, and at least two of the R1 to R4 groups denote hydrogen;

R5 denotes hydrogen, a halogen atom (F, Cl, Br, I), a $C_1$–$C_4$-alkyl, $C_1$–$C_4$-hydroxyalkyl or $C_1$–$C_4$-alkoxy group;

R6 and R7 independently of each other denote hydrogen, a halogen atom (F, Cl, Br, I), a nitro, $C_1$–$C_4$-alkoxy, $C_1$–$C_6$-alkyl, $C_1$–$C_4$-hydroxyalkyl or $C_3$–$C_4$ dihydroxyalkyl group or a group of formula (II):

(II)

and R8 denotes hydrogen, an amino group, a halogen atom (F, Cl, Br, I), a nitro group or a hydroxyl group.

Suitable compounds of formula (I) are, for example, the following:

1,4-diamino-2-(thiazol-2-yl)benzene; 1,4-diamino-2-(4-methylthiazol-2-yl)benzene; 1,4-diamino-2-(5-methylthiazol-2-yl)benzene; 1,4-diamino-2-(4-chlorothiazol-2-yl)-benzene; 1,4-diamino-2-(5-chlorothiazol-2-yl)benzene; 1,4-diamino-2-(5-nitrothiazol-2-yl)benzene; 1,4-diamino-2-(4,5-dimethylthiazol-2-yl)benzene; 1,4-diamino-2-[4-methyl-5-(2-hydroxyethyl)thiazol-2-yl]benzene; 1,4-diamino-2-(4-phenylthiazol-2-yl)-benzene; 1,4-diamino-2-(5-nitrothiazol-2-yl)benzene; 1,4-diamino-2-(5-phenylthiazol-2-yl)benzene; 1-amino-4-methylamino-2-(thiazol-2-yl)benzene; 1-amino-4-(2-hydroxyethyl)amino-2-(thiazol-2-yl)benzene and 1-amino-4-bis(2-hydroxyethyl)amino-2-(thiazol-2-yl)benzene.

Preferred are compounds of formula (I) wherein (i) one or more of groups R5, R6 and R7 denote hydrogen and/or (ii) R1, R2, R3 and R4 at the same time denote hydrogen and/or (iii) one or both R6 and R7 groups denote $C_1$–$C_4$-alkyl or $C_1$–$C_4$-hydroxyalkyl.

In particular, the following compounds should be mentioned:

1,4-diamino-2-(thiazol-2-yl)benzene; 1,4-diamino-2-(4,5-dimethylthiazol-2-yl)benzene; 1,4-diamino-2-(4-phenylthiazol-2-yl)benzene and 1,4-diamino-2-(4-methylthiazol-2-yl)benzene.

The compounds of formula (I) can be used as free bases or in the form of their physiologically tolerated salts with inorganic or organic acids, for example hydrochloric acid, sulfuric acid, phosphoric acid, acetic acid, propionic acid, lactic acid or citric acid.

The 1,4-diamino-2-(thiazol-2-yl)benzene derivatives of formula (I) of the invention can be prepared by known methods of synthesis. For example, the synthesis of the compounds of the invention can be carried out as follows: a) by tetrakis-(triphenylphosphine)palladium(0)-catalyzed coupling of a substituted benzene of formula (III):

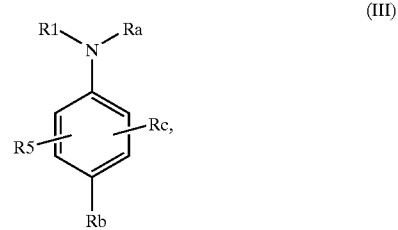

(III)

with a heteroaryl compound of formula (IV):

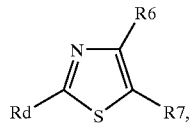

(IV)

wherein
Ra denotes a protective group, as described, for example, in the chapter on "Protective Groups" in Organic Synthesis, chapter 7, Wiley Interscience, 1991,
Rb denotes NR1Ra or $NO_2$,
Rc denotes halogen, and Rd denotes $B(OH)_2$, or Rc denotes $B(OH)_2$ and Rd denotes halogen, and
R1, R5, R6, R7 and R8 have the same meaning as in formula (I), followed by removal of the protective group or by removal of the protective group and reduction of the nitro group;
or b) by a tetrakis(triphenylphosphine)palladium(0)-catalyzed coupling of a substituted benzene of formula (V):

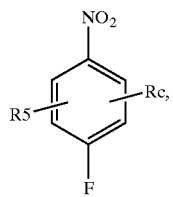

(V)

with the heteroaryl compound of formula (IV):

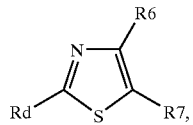

(IV)

wherein
Rc denotes halogen and Rd denotes $B(OH)_2$ or Rc denotes $B(OH)_2$ and Rd denotes halogen, and
R5, R6 and R7 have the same meaning as in formula (I), followed by substitution of the resulting substituted benzene of formula (VI):

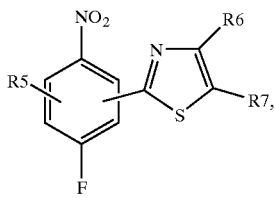

(VI)

with an amine of formula HNR1R2,
wherein R1, R2 have the same meaning as in formula (I), followed by reduction of the nitro group.

The 1,4-diamino-2-(thiazol-2-yl)benzene derivatives of formula (I) are readily water-soluble and produce colorations of high color intensity and excellent color fastness, particularly in terms of light fastness, wash fastness and rubbing fastness. The compounds of formula (I) also show outstanding storage stability, particularly as constituents of the colorants described in the following.

Hence, another object of the present invention are agents for oxidative dyeing of keratin fibers, for example hair, furs, feathers or wool, particularly human hair, based on a developer-coupler combination containing as the developer at least one 1,4-diamino-2-(thiazol-2-yl)benzene derivative of formula (I).

The colorant of the invention contains the 1,4-diamino-2-(thiazol-2-yl)benzene derivative of formula (I) in an amount from about 0.005 to 20 wt. %, an amount of about 0.01 to 5.0 wt. % and especially 0.1 to 2.5 wt. % being particularly preferred.

Preferred couplers are: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]-aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4[2H]benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Although, because of the advantageous properties of the 1,4-diamino-2-(thiazol-2-yl)-benzene derivatives of formula (I) described herein, it would be obvious to use these derivatives as the only developers, it is, of course, also possible to use the 1,4-diamino-2-(thiazol-2-yl)benzene derivatives of formula (I) together with known developers, for example with 1,4-diaminobenzene, 2,5-diaminotoluene, 2,5-diaminophenylethyl alcohol, 4-aminophenol and derivatives thereof, for example 4-amino-3-methylphenol, 4,5-diamino-1-[2-hydroxyethyl)pyrazole, 4,5-diamino-1-benzylpyrazole, 4,5-diamino-1-(4-methylbenzylpyrazole or tetraaminopyrimidines.

The couplers and developers can be present in the colorant of the invention either individually or in admixture with one another, the total amount of each of the couplers and developers in the colorant of the invention being about 0.005 to 20 wt. % preferably about 0.01 to 5.0 wt. % and particularly 0.1 to 2.5 wt. % (based on the total amount of colorant).

The total amount of the developer-coupler combination contained in the colorant described herein is preferably about 0.01 to 20 wt. %, an amount of about 0.02 to 10 wt. % and especially 0.2 to 6.0 wt. % being particularly preferred. In general, the developer and the coupler are used in approximately equimolar amounts; however, it is not disadvantageous if the developer is present in a certain excess or deficiency.

Moreover, the colorant of the invention can also contain other dye components, for example 6-amino-2-methylphenol and 2-amino-5-methylphenol, as well as common direct dyes, for example triphenylmethane dyes such as 4-[(4'-aminophenyl)-(4''-imino-2'',5''-cyclohexadien-1''-ylidene)methyl]-2-methylaminobenzene monohydrochloride (Color Index [C.I.] 42 510) and 4-[(4'-amino-3'-methylphenyl)-(4''-imino-3''-methyl-2'',5''-cyclohexadien-1''-ylidene)methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenoland 1-(2'-ureidoethyl)amino-4-nitrobenzene, azo dyes such as, for example, sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain these dyes in an amount from about 0.1 to 4.0 wt. %.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants are to be used for coloring hair, they can also contain other common cosmetic additives, for example antioxidants such as ascorbic acid, thioglycolic acid or sodium sulfite, as well as perfume oils, complexing agents, wetting agents, emulsifiers, thickeners and hair-care agents. The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 25 wt. % and the hair-care agents at a concentration from about 0.1 to 5.0 wt. %.

Depending on the composition, the colorant of the invention can be weakly acidic, neutral or alkaline. In particular, it has a pH of about 6.5 to 11.5. Adjustment to a basic pH is preferably done with ammonia, but it can also be done with an organic amine, for example monoethanolamine and triethanolamine, or with an inorganic base such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorant is mixed with an oxidant just before use, and the resulting mixture is applied to hair in an amount sufficient for the hair-dyeing treatment, in general about 60 to 200 grams, depending on the hair fullness.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a 1,4-diamino-2-(thiazol-2-yl)benzene derivative of formula (I) as developer give keratin, and particularly hair, colorations of excellent color fastness, particularly in terms of light fastness, wash fastness and rubbing fastness. As far as the dyeing properties are concerned, the hair colorants of the invention provide a wide range of different color shades from blond to brown, purple, violet and even blue and black, depending on the kind and composition of the dye components. These shades have unusual color intensity. The very good coloring properties of the hair colorants of the present patent application also manifest themselves in that these colorants make it possible to dye hair, previously not damaged chemically, without any problems and with good covering power.

The following examples illustrate the object of the invention in greater detail without limiting its scope.

EXAMPLES

Example 1

Synthesis of 1,4-diamino-2-(thiazol-2-yl)benzene
A. Synthesis of N,N'-bis(tert.butoxycarbonyl)-2,5-diamino-1-phenylboric acid N,N'-bis(tert.Butoxycarbonyl)-2,5-diamino-1-phenylboricacid is obtained by reaction of N,N'-bis(tert.butoxycarbonyl)-2,5-diamino-1-bromobenzene with tert.butyllithium and trimethyl borate. Experimental details of this method of preparation are described by J. M. Tour and J. J. S. Lamba in J. Am. Chem. Soc. 1994, 116, page 11723, B. Synthesis of 1,4-diamino-2-(thiazol-2-yl)benzene hydrochloride 0.035 g (0.0001 mole) of N,N'-bis(tert.butyloxycarbonyl)-2,5-diamino-1-phenylboric acid from step A and 0.00015 mole of 2-bromothiazole were dissolved in 10 mL of 1,2-dimethoxyethane under argon. Then, 0.005 g of tetrakis(triphenylphosphine)-palladium (0.000005 mole) and 0.13 mL of a 2-normal potassium carbonate solution were added, and the reaction mixture was heated to 80° C. At the end of the reaction, the reaction mixture was poured into 10 mL of ethyl acetate, and the organic phase was extracted with dilute sodium hydroxide solution and then dried over magnesium sulfate. The solvent was distilled off in a rotary evaporator, and the residue was purified on silica gel with petroleum ether/ethyl acetate (9:1). The product thus obtained was dissolved in 4 mL of ethanol and heated to 50° C. Then, to prepare the hydrochloride, 1.5 mL of a 2.9-molar ethanolic hydrochloric acid solution was added dropwise. The precipitate was filtered off, washed twice with 1-mL portions of ethanol and then dried.

Yield: 0.015 g (94% of the theoretical).
Mass spectrum: MH$^+$ 192(100).

Example 2

Hair Colorants

Hair colorant solutions having the following composition were prepared:

| | |
|---|---|
| 1.25 mmoles | of 1,4-diamino-2-(thiazol-2-yl)benzene.HCl |
| 1.25 mmoles | of coupler according to Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| Coupler | Coloration |
|---|---|
| a) 1,3-Dihydroxybenzene | dark-blond |
| b) 1,3-Diamino-4-(2-hydroxyethoxy)-benzene sulfate | dark-blue |
| c) 5-Amino-2-methylphenol | purple |
| d) 1-Naphthol | blue |

Examples 3 to 12

Hair Colorants

Hair colorant solutions of the following composition were prepared:

| | |
|---|---|
| X g | of 1,4-diamino-2-(thiazol-2-yl)benzene.HCl (E1) |
| U g | of developer E8 to E15 as per Table 2 |
| Y g | of coupler K11 to K36 as per Table 4 |
| Z g | of direct dye D1 to D3 as per Table 3 |
| 10.0 g | of potassium oleate (8% aqueous solution) |
| 10.0 g | of ammonia (22% aqueous solution) |
| 10.0 g | of ethanol |
| 0.3 g | of ascorbic acid |
| to 100.0 g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 5 shows the coloring results.

Examples 13 to 18

Hair Colorants

Dye carriers in cream form and having the following composition were prepared:

| | |
|---|---|
| X g | of 1,4-diamino-2-(thiazol-2-yl)benzene.HCl (E1) |
| U g | of developer E8 to E15 as per Table 2 |
| Y g | of coupler K11 to K36 as per Table 4 |
| Z g | of direct dye D2 as per Table 3 |
| 15.0 g | of cetyl alcohol |
| 0.3 g | of ascorbic acid |
| 3.5 g | of sodium lauryl alcohol diethylene glycol ether sulfate, 28% aqueous solution |
| 3.0 g | of ammonia, 22% aqueous solution |
| 0.3 g | of sodium sulfite, anhydrous |
| to 100.0 g | water |

Just before use, 30 g of the foregoing coloring cream was mixed with 30 g of a 6% aqueous solution of hydrogen peroxide. The mixture was then applied to the hair. After an exposure time of 30 min at 40° C., the hair was rinsed with water, washed with a commercial shampoo and dried. The coloring results are presented in Table 6.

TABLE 2

| Developers | |
|---|---|
| E1 | 1,4-diamino-2-(thiazol-2-yl)lbenzene.HCl |
| E8 | 1,4-diaminobenzene |
| E9 | 2,5-diaminophenylethanol sulfate |
| E10 | 3-methyl-4-aminophenol |
| E11 | 4-amino-2-aminomethylphenol dihydrochloride |
| E12 | 4-aminophenol |
| E13 | N,N-bis(2'-hydroxyethyl)-p-phenylenediamine sulfate |
| E14 | 4,5-diamino-1-(2'-hydroxyethyl)pyrazole sulfate |
| E15 | 2,5-diaminotoluene sulfate |

TABLE 3

| Direct Dyes | |
|---|---|
| D1 | 2,6-diamino-3-[(3-pyridinyl)azo]pyridine |
| D2 | 6-chloro-2-ethylamino-4-nitrophenol |
| D3 | 2-amino-6-chloro-4-nitrophenol |

TABLE 4

| | Couplers |
|---|---|
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis(2,4-diaminophenoxy)propane tetrahydrochloride |
| K21 | 3-aminophenol |
| K22 | 5-amino-2-methylphenol |
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylenedioxybenzene hydrochloride |
| K35 | 3,4-methylenedioxyphenol |
| K36 | 2-amino-5-methylphenol |

TABLE 5

Hair Colorants

| | Example No. | | | |
|---|---|---|---|---|
| Dyes | 3 | 4 | 5 | 6 |
| | (Dyes in grams) | | | |
| E1 | 0.25 | 0.20 | 0.20 | 0.20 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Coloring results | red-brown | red-brown | red-brown | red-brown |

| | Example No. | | | | | |
|---|---|---|---|---|---|---|
| Dyes | 7 | 8 | 9 | 10 | 11 | 12 |
| | (Dyes in grams) | | | | | |
| E1 | 0.35 | 0.25 | 0.30 | 0.10 | 0.10 | 0.15 |
| E8 | | | 0.15 | | | |
| E9 | | | | 0.15 | | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring result | blond | blond | blond | blond | blond | blond |

TABLE 6

Hair Colorants

| | Example No. | | | | | |
|---|---|---|---|---|---|---|
| Dyes | 13 | 14 | 15 | 16 | 17 | 18 |
| | (Dyes in grams) | | | | | |
| E1 | 1.80 | 1.80 | 1.80 | 0.70 | 0.70 | 0.70 |
| K12 | | | | 0.10 | 0.10 | 0.10 |
| K13 | 1.10 | 1.10 | 1.10 | | | |
| K31 | 1.10 | 1.10 | 1.10 | 0.40 | 0.40 | 0.40 |
| D2 | | | | 0.10 | 0.10 | 0.10 |
| K23 | | | 0.05 | 0.10 | 0.10 | 0.10 |
| Coloring results | black | black | black | brown | brown | brown |

Unless otherwise indicated, all percentages given in the present patent application are by weight.

What is claimed is:

1. 1,4-Diamino-2-(thiazol-2-yl)benzene derivatives of formula (I):

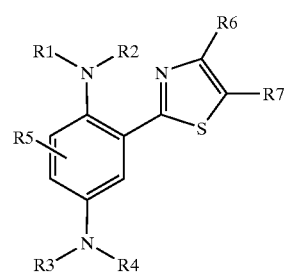

(I)

wherein

R1, R2, R3 and R4 independently of each other denote hydrogen, a $C_1$–$C_6$-alkyl, $C_2$–$C_4$-hydroxyalkyl, $C_3$–$C_4$-dihydroxyalkyl or $C_2$–$C_4$-alkoxy-($C_1$–$C_2$)-alkyl group or R1 and R2 or R3 and R4 form a four-membered to eight-membered aliphatic ring, and at least two of the R1 to R4 groups denote hydrogen;

R5 denotes hydrogen, a halogen atom, a $C_1$–$C_4$-alkyl, $C_1$–$C_4$-hydroxyalkyl or $C_1$–$C_4$-alkoxy group;

R6 and R7 independently of each other denote hydrogen, a halogen atom, a nitro, $C_1$–$C_4$-alkoxy, $C_1$–$C_6$-alkyl, $C_1$–$C_4$-hydroxyalkyl or $C_3$–$C_4$ dihydroxyalkyl group or a group of formula (II)

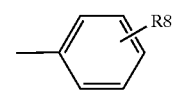

(II)

and R8 denotes hydrogen, an amino group, a halogen atom, a nitro group or a hydroxyl group.

2. 1,4-Diamino-2-(thiazol-2-yl)benzene derivative according to claim 1, characterized in that in formula (I) one or more groups R5 to R7 denote hydrogen.

3. 1,4-Diamino-2-(thiazol-2-yl)benzene derivative according to claim 1, characterized in that in formula (I) groups R1, R2, R3 and R4 denote hydrogen.

4. 1,4-Diamino-2-(thiazol-2-yl)benzene derivative according to claim 1, characterized in that in formula (I) one or both of groups R6 and R7 denote a $C_1$–$C_4$-alkyl group or a $C_1$–$C_4$-hydroxyalkyl group.

5. 1,4-Diamino-2-(thiazol-2-yl)benzene derivative according to one of claims 1 to 4, characterized in that it is selected from among 1,4-diamino-2-(thiazol-2-yl)benzene; 1,4-diamino-2-(4,5-dimethylthiazol-2-yl)benzene; 1,4-diamino-2-(4-phenylthiazol-2-yl)benzene and 1,4-diamino-2-(4-methylthiazol-2-yl)benzene.

6. Agent for oxidative dyeing of keratin fibers based on a developer-coupler combination, characterized in that it contains as developer at least one 1,4-diamino-2-(thiazol-2-yl)benzene derivative of formula (I) according to claim 1.

7. Agent according to claim 6, characterized in that it contains the 1,4-diamino-2-(thiazol-2-yl)benzene derivative of formula (I) in an amount from 0.005 to 20.0 wt %.

8. Agent according to claim 6, characterized in that the coupler is selected from among 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]anilino, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4[2H]-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

9. Agent according to claim 6, characterized in that in addition to the 1,4-diamino-2-(thiazol-2-yl)benzene derivative of formula (I) it contains at least one other developer from the group consisting of 1,4-diaminobenzene, 2,5-diaminotoluene, 2-(2,5-diaminophenyl)ethyl alcohol, 4-aminophenol and derivatives thereof, 4,5-diaminopyrazole derivatives and tetraaminopyrimidines.

10. Agent according to claim 6, characterized in that each of the developers and couplers is present in a total amount of 0.005 to 20 wt %, based on the total amount of oxidation dye.

11. Agent according to claim 6, characterized in that it contains additionally at least one direct dye.

12. Agent according to claim 6, characterized in that it has a pH from 6.5 to 11.5.

13. Agent according to claim 6, characterized in that it is in the form of an aqueous or aqueous-alcoholic solution, a cream, a gel or an emulsion.

14. Agent according to claim 6, characterized in that it is a hair colorant.

* * * * *